United States Patent [19]

Yamamoto et al.

[11] 3,970,654
[45] July 20, 1976

[54] ANTIVIRAL 2(1H)-QUINAZOLINONE DERIVATIVES

[75] Inventors: Michihiro Yamamoto; Shigeaki Morooka, both of Nishinomiya; Masao Koshiba, Amagasaki; Shigeho Inaba, Takarazuka; Hisao Yamamoto, Nishinomiya, all of Japan

[73] Assignee: Sumitomo Chemical Company, Limited, Osaka, Japan

[22] Filed: July 30, 1974

[21] Appl. No.: 493,240

[30] Foreign Application Priority Data

Aug. 14, 1973 Japan.................................. 48-91590

[52] U.S. Cl. .................. 260/251 QB; 260/256.4 Q; 260/256.5 R; 260/294.8 B; 260/294.8 C; 260/295 T; 260/295 K; 260/296 T; 260/296 B; 260/329 S; 260/329 F; 260/562 B; 260/571; 260/576; 424/251

[51] Int. Cl.² ...................................... C07D 239/82

[58] Field of Search ............. 260/251 QB, 256.4 Q, 260/256.5 R

[56] References Cited
UNITED STATES PATENTS

| | | | |
|---|---|---|---|
| 3,712,892 | 1/1973 | Inaba et al..................... | 260/251 QB |
| 3,748,342 | 7/1973 | Cooke et al.................. | 260/332.3 P |
| 3,859,237 | 1/1975 | Inaba et al..................... | 260/251 QB |

*Primary Examiner*—Raymond V. Rush
*Attorney, Agent, or Firm*—Stevens, Davis, Miller & Mosher

[57] ABSTRACT

Quinazolinone derivatives of the formula,

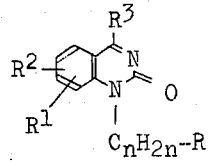

wherein R is a polyalicyclic hydrocarbon group; $R^1$ and $R^2$ are independently a hydrogen atom, a nitro group, a trifluoromethyl group or a methylsulfonyl group; $R^3$ is a phenyl group, a substituted phenyl group, a pyridyl group or a thienyl group; and $n$ is 0 or an integer of 1 to 3, have potent antiviral activity with low toxicities. These compounds can be prepared using a variety of processes analogous to known methods, for example, by oxidizing a 3,4-dihydro-2(1H)-quinazolinone having a polyalicyclic hydrocarbon group bonded through an alkylene group at the 1 position.

5 Claims, No Drawings

ANTIVIRAL 2(1H)-QUINAZOLINONE DERIVATIVES

This invention relates to novel quinazolinone derivatives, and methods of preparing the same. More particularly, the invention pertains to novel 2(1H)-quinazolinone derivatives represented by the formula,

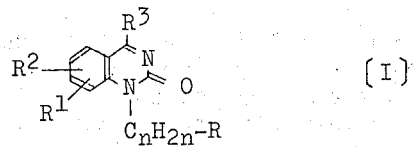

wherein R is a polyalicyclic hydrocarbon group; $R^1$ and $R^2$ are independently a hydrogen atom, a nitro group, a trifluoromethyl group or a methylsulfonyl group; $R^3$ is a phenyl group, a substituted phenyl group, a pyridyl group or a thienyl group; and $n$ is 0 or an integer of 1 to 3, and to processes for production and pharmaceutical use of the same.

In the compounds represented by the general formula [I], the term polyalicyclic hydrocarbon group means bicyclic or tricyclic saturated or unsaturated alicyclic hydrocarbon radicals which contains 4 to 14 carbon atoms, such as 1-adamantyl, 2-adamantyl, 1-noradamantyl, 9-noradamantyl, 1norbornyl, 2-norbornyl, 2-methyl-2-norbornyl, 7-norbornyl, 2-bicyclo[1,1,0]butyl, 5-bicyclo[2,1,0]pentyl, 6-bicyclo[3,1,0]hexyl, 7-bicyclo-[4,1,0]heptyl, 1-bicyclo[2,1,1]hexyl, 6,6-dimethylbicyclo-[3,1,1]hept-2-ene-2-yl, 1-bicyclo[2,2,2]octyl, 2-bicyclo-[2,2,2]octyl, bicyclo[2,2,2]oct-5-ene-2-yl, 1-bicyclo-[3,2,1]octyl, 6-methyl-2-bicyclo[3,2,1]octyl, 3-bicyclo-[3,3,0]octyl, 3-bicyclo[3,3,1]nonyl, 6-bicyclo[3,2,2]-nonyl, 8-bicyclo[4,3,0]nonyl, 1-bicyclo[4,4,0]decyl, 3-bicyclo[4,4,0]decyl, 5-methyl-1-tricyclo[3,2,2,0$^{2,4}$]-nonyl, and the like. The phenyl group in the 4 position may be substituted by halogen, nitro, trifluoromethyl, methoxy or methyl. The alkylene group represented by the formula $C_nH_{2n}$ includes a straight chain or branched chain alkylene such as methylene, ethylene, 1-methylethylene, 2-methylethylene or trimethylene.

Preferred compounds falling within the formula [I] have the substituents wherein $R^1$ is a hydrogen atom; $R^2$ is a nitro group; $R^3$ is a phenyl group; R is a polyalicyclic $C_{7-10}$ hydrocarbon group; and $n$ is 1.

The quinazolinone derivatives of the formula [I] are found to have potent antiviral activity with low toxicities. Particularly these compounds may be effectively employed to control viral infections caused by the viruses belonging to the Pox, group. More particularly, these compounds have exhibited remarkable antiviral activities against the vaccinia virus belonging to the Pox group.

Thus the present invention provides novel quinazolinone derivatives which are valuable as antiviral agents, and processes for preparing the same.

These quinazolinone derivatives can be prepared using a variety of processes analogous to known methods as described below.

One method for preparing the compounds of the formula [I], comprises contacting a compound of the formula,

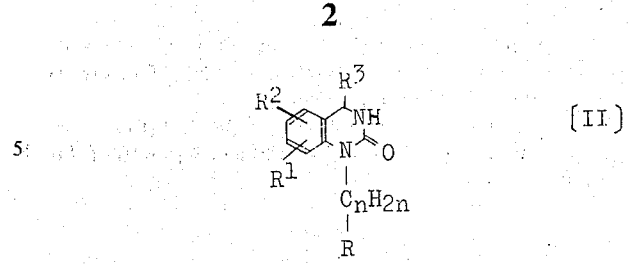

wherein $R^1$, $R^2$, $R^3$, n and R are as defined above, with an oxidizing agent.

Suitable oxidizing agents include, for example, potassium permanganate, sodium permanganate, manganese dioxide, chromium trioxide, magnesium dioxide and sodium metaperiodate.

The reaction may be carried out in the presence of an inert solvent or a solvent mixture.

Examples of the solvent include benzene, toluene, ether, tetrahydrofuran, dioxane, chloroform, carbon tetrachloride, acetone, methanol, ethanol, isopropanol, acetic acid, dimethylformamide, dimethyl sulfoxide and water and a mixture thereof.

The reaction is generally effected at a temperature in the range between about room temperature and the boiling point of the solvent employed.

The compound of the formula [II] can be obtained by reacting a compound of the formula,

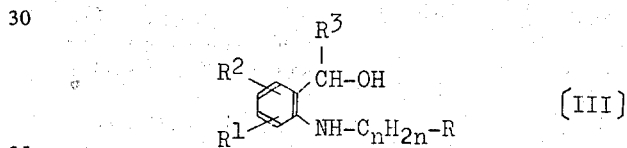

wherein $R^1$, $R^2$, $R^3$, n and R are as defined above, with a carbamic acid ester or carbamic acid halide, cyanic acid or a salt thereof or urea. The reaction may be effected by heating a compound of the formula [III] with a carbamic acid ester (e.g. methyl carbamate, ethyl carbamate or benzyl carbamate) or a carbamic acid halide (e.g. carbamyl chloride) in the presence of a Lewis acid such as zinc chloride, otherwise with cyanic acid or a salt thereof (e.g. sodium cyanate or potassium cyanate) or urea in the presence of an acidic solvent such as acetic acid.

Another method comprises reacting a compound of the formula,

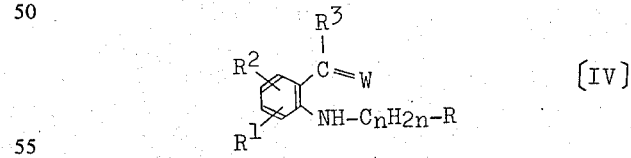

wherein $R^1$, $R^2$, $R^3$, n and R are as defined above, and W is an oxygen atom or an imino group, with a carbamic acid ester, a carbamic acid halide, cyanic acid or a salt thereof or urea.

The reaction may be carried out by reacting a compound of the formula [IV] with a carbamic acid ester or a carbamic acid halide in the presence of a Lewis acid such as zinc chloride, otherwise with cyanic acid or a salt thereof or urea in the presence of a solvent such as acetic acid.

The reaction temperature may vary from about 100°C to about 200°C depending on the NCO group containing compound employed.

A further method for synthesis of the compounds of the formula [I], comprises reacting a compound of the formula,

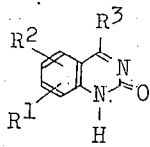   [V]

wherein R¹, R² and R³ are as defined above, with a reactive ester of a compound of the formula,

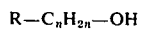   [VI]

wherein n and R are as defined above. The reaction may be carried out by reacting a compound of the formula [V] with a reactive ester of the compound of the formula [VI] in the presence of a condensing agent, or alternatively by treating the compound of the formula [V] with a condensing agent in a solvent to form a metal salt and then reacting the metal salt with the reactive ester of the compound of the formula [VI].

As the reactive ester of the compound of the formula [VI], there may be preferably used a hydrohalic acid ester such as chloride, bromide or iodide, or a sulfonic acid ester such as methanesulfonic acid ester, trichloromethanesulfonic acid ester or p-toluenesulfonic acid ester.

Suitable condensing agents include, for example, sodium hydride, potassium hydride, sodium amide, potassium amide, butyllithium, phenyllithium, sodium methylate, potassium methylate, sodium ethylate, potassium ethylate and mercuric chloride.

Suitable solvents include, for example, aromatic hydrocarbons such as benzene, toluene, xylene, monochlorobenzene; amides such as dimethylacetamide, diethylacetamide, dimethylformamide; ethers such as diethylether, tetrahydrofuran, dioxane; and dimethyl sulfoxide. The choice of the solvent may depend on the reactive ester and the condensing agent employed.

The reaction is generally effected at a temperature in the range between room temperature and the boiling point of the solvent used.

The reaction may be accompanied by formation of the quinazoline derivatives of the formula,

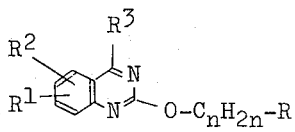   [VII]

wherein R¹, R², R³, n and R are as defined above.

The separation of the desired compound of the formula [I] from the compound of the formula [VII] may be effected using conventional techniques, for example, by chromatography or fractional crystallization.

A still further method for preparing the compounds of the formula [I], comprises reacting a compound of the formula,

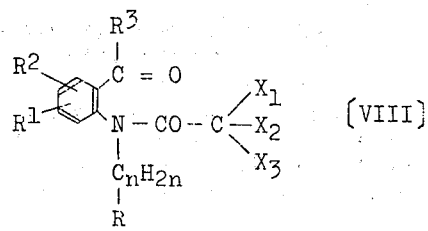   [VIII]

wherein R¹, R², R³, n and R are as defined above; and X₁, X₂ and X₃ are each a halogen atom, with ammonia.

The reaction may be carried out in the presence of a solvent or solvent mixture. Examples of the solvent include methanol, ethanol, isopropanol, tertiary-butanol, 2-ethoxyethanol, tetrahydrofuran, dioxane, acetone, pyridine, benzene, toluene, dimethylsulfoxide and dimethylformamide and mixture thereof. Ammonia is added to the reaction mixture as gaseous ammonia, alcoholic ammonia (e.g. methanolic or ethanolic ammonia), liquid ammonia or ammonium salt (e.g. ammonium acetate, ammonium formate, ammonium carbamate or ammonium succinate) which generates ammonia during the reaction. The reaction generally proceeds at room temperature, and if desired, may be controlled appropriately by adopting a higher or lower temperature.

The starting compounds of the formula [VIII] are novel and also useful as intermediates for synthesis of other quinazoline derivatives. They can be conveniently obtained by reacting a compound of the formula,

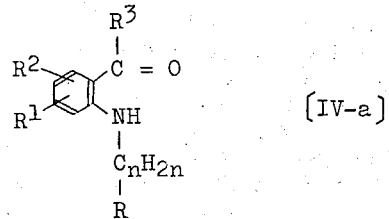   [IV-a]

wherein R¹, R², R³, n and R are as defined above, with a trihalogenoacetic acid, or a reactive derivative thereof, represented by the formula,

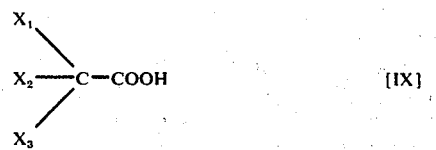   [IX]

wherein X₁, X₂ and X₃ are as defined above. Examples of the reactive derivatives of the trihalogenoacetic acid include acid halides and acid anhydrides.

The other method for preparing the compound of the formula [I] comprises reacting a compound of the formula,

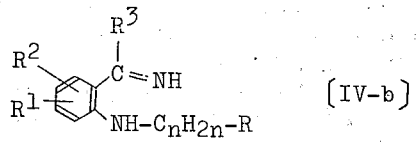   [IV-b]

wherein $R^1$, $R^2$, $R^3$, n and R are as defined above, with a carbonic acid derivative of the formula,

 [X]

wherein Y and Z are each a chlorine atom, a $C_{1-4}$ alkoxy group, a benzyloxy group, a $C_{1-4}$ alkylthio group, a trichloromethyl group or a 1-imidazolyl group.

The reaction may be carried out in the presence or absence of an inert solvent and a basic condensing agent.

As the carbonic acid derivative of the formula [X], there may be preferably used phosgene, methyl chlorocarbonate, ethyl chlorocarbonate, isopropyl chlorocarbonate, benzyl chlorocarbonate, ethyl chlorothiolformate, trichloroacetyl chloride, hexachloroacetone or 1,1'-carbonyldiimidazole.

Suitable solvents include, for example, benzene, toluene, xylene, chlorobenzene, pyridine, diethyl ether, isopropyl ether, tetrahydrofuran, dioxane, chloroform, dichloroethane, dimethylformamide and the like.

Suitable basic condensing agents include, for example, inorganic bases such as sodium hydroxide, potassium hydroxide, sodium carbonate or potassium carbonate, and tertiary amines such as triethylamine, N,N-dimethylaniline or pyridine.

The reaction temperature may vary from about room temperature to the boiling point of the solvent, depending on the carbonic acid derivative employed.

According to the processes of the present invention, there are obtained, for example, the following quinazolinone derivatives;

1-(1-adamantylmethyl)-4-phenyl-6-nitro-2(1H)-quinazolinone
1-(1-adamantylmethyl)-4-(2-pyridyl)-6-nitro-2(1H)-quinazolinone
1-(1-adamantylmethyl)-4-(2-thienyl)-6-nitro-2(1H)-quinazolinone
1-(1-adamantylmethyl)-4-phenyl-6-trifluoromethyl-2(1H)-quinazolinone
1-(1-adamantylmethyl)-4-phenyl-6-methylsulfonyl-2(1H)-quinazolinone
1-(2-adamantylmethyl)-4-phenyl-6-nitro-2(1H)-quinazolinone
1-(1-noradamantylmethyl)-4-phenyl-6-nitro-2(1H)-quinazolinone
1-(9-noradamantylmethyl)-4-phenyl-6-nitro-2(1H)-quinazolinone
1-(2-norbornylmethyl)-4-phenyl-6-nitro-2(1H)-quinazolinone
1-(7-norbornylmethyl)-4-phenyl-6-nitro-2(1H)-quinazolinone
1-(norbornadien-7-ylmethyl)-4-phenyl-6-nitro-2(1H)-quinazolinone
1-[2-(1-norbornyl)ethyl]-4-phenyl-6-nitro-2(1H)-quinazolinone
1-(6-bicyclo[3,1,0]hexylmethyl)-4-phenyl-6-nitro-2(1H)-quinazolinone
1-(1-bicyclo[2,1,1]hexylmethyl)-4-phenyl-6-nitro-2(1H)-quinazolinone
1-[2-(6,6-dimethylbicyclo[3,1,1]hept-2-ene-2-yl)ethyl]-4-phenyl-6-nitro-2(1H)-quinazolinone
1-(1-bicyclo[2,2,2]octylmethyl)-4-phenyl-6-nitro-2(1H)-quinazolinone
1-(bicyclo[2,2,2]oct-5-ene-2-ylmethyl)-4-phenyl-6-nitro-2(1H)-quinazolinone
1-(1-bicyclo[3,2,1]octylmethyl)-4-phenyl-6-nitro-2(1H)-quinazolinone
1-(1-bicyclo[3,3,0]octylmethyl)-4-phenyl-6-nitro-2(1H)-quinazolinone
1-(3-bicyclo[3,3,1]nonylmethyl)-4-phenyl-6-nitro-2(1H)-quinazolinone
1-(8-bicyclo[4,3,0]nonylmethyl)-4-phenyl-6-nitro-2(1H)-quinazolinone
1-(1-bicyclo[14,4,0]decylmethyl)-4-phenyl-6-nitro-2(1H)-quinazolinone The present compounds may be used in the form of pharmaceutical preparations for human use against the vaccinia virus belonging to the Pox group which are applied by either enteral or parenteral administration. Preferable excipients used therein are those which do not react with the compounds mentioned, for example, water, gelatine, lactose, starch, stearic acid, magnesium stearate, talc, white petroleum jelly, vegetable oils, alcohol, benzyl alcohol, gums, polyalkylene glycols, or other known excipients for medicines. The pharmaceutical preparations may be in the form of tablets, powder, dragees (sugar coated tablets), capsules, suppositories, liquids, elixirs, emulsions, suspensions, syrups, chocolate, candy, waters, chewing gum or the like. If desired, they are sterilised and/or contain auxiliary substances such as preservatives, stabilisers, wetting agents, detergents or buffers. They may also additionally contain other therapeutically valuable substances (e.g. other antiviral agents, chemotherapeutic agents, antibiotics, anti-inflammatory agents, anti-pyretics, analgesics, enzyme preparations or the like).

The preparations are formulated by the usual methods. They may be cojointly administered with a viral inhibitor such as interferon, interferon inducer or the like. The compositions and preparations should contain at least 0.1% of active component. The amount of active component in these useful compositions or preparations is such that a suitable dosage of 0.2 mg to 200 mg/kg/day will be obtained.

This invention is further disclosed in the following examples of more preferred embodiments thereof, which are presented for the purpose of illustration and it is not intended to limit the scope of the invention.

EXAMPLE 1

To a solution of 3.8 g of 1-(1-adamantylmethyl)-4-phenyl-6-nitro-3,4-dihydro-2(1H)-quinazolinone in 70 ml of dioxane was added a suspension of 1.5 g of potassium permanganate in 10 ml of water and the mixture was stirred at room temperature for 3 hours. Then, 7 ml of formic acid was added and stirring was continued for 30 minutes. The brown precipitate was filtered off and the filtrate was diluted with water. The resulting mixture was extracted with chloroform. The chloroform extract was washed, dried over anhydrous sodium sulfate and concentrated in vacuo. The residue was crystallized from a mixture of ethanol and chloroform to give 1-(1-adamantylmethyl)-4-phenyl-6-nitro-2(1H)-quinazolinone, m.p. 228°–231°C.

EXAMPLE 2

A mixture of 3.9 g of 2-(1-adamantylmethyl-amino)-5-nitrobenzophenone, 6.4 g of ethyl carbamate and 0.45 g of anhydrous zinc chloride was heated at 170°–180°C for 1 hour, and then, distillating off the produced ethanol, heating was continued at that temperature for additional 1 hour. After cooling, chloroform was added thereto and insoluble material was filtered off. The chloroform layer was washed with water and dried over anhydrous sodium sulfate. The solvent was removed under reduced pressure and the residual oil was chromatographed on silica gel using chloroform as eluting solvent to give 1-(1-adamantylmethyl)-4-phenyl-6-nitro-2(1H)-quinazolinone, m.p. 230°– 233°C, following recrystallization from a mixture of ethanol and chloroform.

EXAMPLE 3

To a suspension of 11 g of 4-phenyl-6-nitro-2(1H)-quinazolinone in 100 ml of dimethylformamide, was added 2.2 g of 52.9% sodium hydride. After stirring at 50°C for 1 hour, 17 g of 2-bromomethyl norbornane was added and the reaction mixture was heated under reflux for 8 hours. After cooling, the mixture was poured into 1 l of water and the resulting mixture was extracted with chloroform. The chloroform layer was washed with water and dried over anhydrous sodium sulfate. The solvent was removed under reduced pressure. The residual oil was chromatographed on silica gel using chloroform as eluting solvent to obtain 1-(2-norbornylmethyl)-4-phenyl-6-nitro-2(1H)-quinazolinone and 2-(2-norbornylmethoxy)-4-phenyl-6-nitroquinazoline. The former was recrystallized from a mixture of carbon tetrachloride and diethyl ether, to give yellow needles, m.p. 160°– 161°C, and the latter was recrystallized from methylchloroform, to give yellow needles, m.p. 153°– 155°C.

EXAMPLE 4

To a solution of 2.5 g of 2-[N-(2-norbornylmethyl)-trichloroacetamido]-5-nitrobenzophenone in 50 ml of tert-butyl alcohol was added 2 g of ammonium acetate and the resulting mixture was heated under reflux for 7 hours. Then 2 g of ammonium acetate was added thereto and the reaction was continued for additional 8 hours. The solvent was removed under reduced pressure, and the residue was extracted with chloroform. The chloroform extract was washed with water, dried over anhydrous sodium sulfate, and evaporated to dryness. The residual oil was crystallized from a mixture of carbon tetrachloride and diethyl ether to give 1-(2-norbornylmethyl)-4-phenyl-6-nitro-2(1H)-quinazolinone, m.p. 160°C.

EXAMPLE 5

To a solution of 3.9 g of 2-(6,6-dimethylbicyclo[3,1,1]hept-2-ene-2-yl) ethylamino-5-nitrobenzophenoneimine and 12 ml of triethylamine in 100 ml of benzene was added dropwise at 5°– 10°C, 70 ml of 10% phosgene solution in benzene and the resulting mixture was stirred at room temperature for 3 hours. The solvent was then removed under reduced pressure, and to the residue was added chloroform and dilute aqueous sodium carbonate with ice-cooling. The chloroform layer was separated, washed with water, dried over anhydrous sodium sulfate and evaporated to dryness. The residual oil was crystallized from ethanol to give 1-[2-(6,6-dimethylbicyclo[3,1,1]hept-2-ene-2-yl)ethyl]-4-phenyl-6-nitro-2(1H)-quinazolinone, m.p. 80°– 81°C.

EXAMPLE 6

Using a procedure similar to that described in Example 3, but replacing 2-bromomethylnorbornane by 2-(6,6-dimethylbicyclo[3,1,1]hept-2-ene-2-yl)-ethylbromide, there were obtained 1-[2-(6,6-dimethylbicyclo[3,1,1]hept-2-ene-2-yl)ethyl]-4-phenyl-6-nitro-2(1H)-quinazolinone, m.p. 79°– 81°C and 2-[2-(6,6-dimethylbicyclo[3,1,1]hept-2-ene-2-yl)ethoxy]-4-phenyl-6-nitroquinazoline, m.p. 106°– 107°C.

What is claimed is:

1. A quinazolinone of the formula,

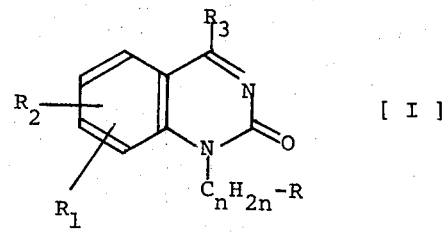

[ I ]

wherein R is bicyclic or tricyclic saturated alicyclic $C_{7-10}$ hydrocarbon radical; $R_1$ is hydrogen; $R_2$ is nitro; $R_3$ is phenyl; and $n$ is 0, 1 or 2.

2. A quinazolinone according to claim 1 wherein $n$ is 1.

3. A quinazolinone according to claim 2, wherein R is adamantyl or norbornyl.

4. A compound according to claim 3 which is 1-(1-adamantylmethyl)-4-phenyl-6-nitro-2(1H)-quinazolinone.

5. A compound according to claim 3 which is 1-(2-norbornylmethyl)-4-phenyl-6-nitro-2(1H)-quinazolinone.

* * * * *